United States Patent
Suh (10) Patent No.: US 6,500,143 B2
(45) Date of Patent: Dec. 31, 2002

(54) BREAST PUMP

(76) Inventor: Kyoung Duk Suh, 301 ho 1-6 Samjun dong Songpa gu, Seoul (KR)

(*) Notice: Subject to any disclaimer, the term of this patent is extended or adjusted under 35 U.S.C. 154(b) by 0 days.

(21) Appl. No.: 09/828,860

(22) Filed: Apr. 10, 2001

(65) Prior Publication Data

US 2001/0047148 A1 Nov. 29, 2001

(30) Foreign Application Priority Data

Apr. 19, 2000 (KR) .............................. 00-21771

(51) Int. Cl.[7] .................................. A61M 1/06
(52) U.S. Cl. .................. 604/73; 604/74; 119/14.01; 119/14.24
(58) Field of Search ............... 604/73, 74; 239/526; 119/14.01, 14.24

(56) References Cited

U.S. PATENT DOCUMENTS

| | | | | |
|---|---|---|---|---|
| 3,382,867 A | * | 5/1968 | Reaves | 601/14 |
| 4,011,838 A | * | 3/1977 | Nordegren et al. | 119/14.08 |
| 5,295,957 A | * | 3/1994 | Aida et al. | 604/74 |
| 5,810,772 A | * | 9/1998 | Niederberger | 604/346 |

* cited by examiner

Primary Examiner—Lesley D. Morris
Assistant Examiner—John Fristoe
(74) Attorney, Agent, or Firm—McGuireWoods LLP (57) ABSTRACT

This invention relates to a breast pump which can perform the automatic suction with the following advantages: 1) a breast-milking mother can stop the operation of breast pump immediately, when her breast site feels painful through continual suction, 2) the suction can be immediately made available by re-pushing a switch, thus more convenient to use, 3) since the breast pump has a massage function in addition to the basic suction of human milk, thus removing a breast stiffness in an efficient manner and improve the overall functions of the breast pump, 4) the rapid detachment of the breast pump after use can be accomplished through a suction release value, thus making the separation procedure of breast pump easier, 5) since the induction neck of breast pump is equipped with a separate induction conduit which is extended to the inside of a breast milk bottle, human milk can be directly dropped to the bottle, whereby disinfecting the bottle is unnecessary, and 6) since the breast milk bottle is connected to the main body of the breast pump with a transparent hose, the attachment of the breast pump to the mother's nipple and breast can be easily seen.

7 Claims, 8 Drawing Sheets

BREAST PUMP

BACKGROUND OF THE INVENTION

Field of the Invention

This invention relates to a breast pump used for squeezing human milk with the following advantages:

1) The automatic suction can ensure the convenience in use;

2) The additional massage function can contribute much to diverse performances;

3) Since the suction neck of breast pump is equipped with a soft induction neck designed to cover the breast site, any discomfort during use can be removed, while the breast pump can be easily detached using a suction release valve; and, 4) Since an induction neck is equipped with a separate induction conduit, human milk can be directly dropped to the floor of breast milk bottle, thus preventing the contamination of breast milk bottle; and, 5) Since the breast milk bottle is connected to the main body of breast pump with a transparent hose, the insertion of breast pump to mother's nipple can be directly ascertained by naked eyes.

In general, a breast pump is intended for use to squeeze the first human milk from child-born or forcibly squeeze excessive amount of human milk during lactation. The breast pump is divided into manual and automatic types.

In the case of the manual breast pump, a lactating woman makes a manual pumping process by hands and thus a lot of force is inevitably required with inconvenient usage. To be harmonious with this matter, various types of automatic breast pump have been recently marketed.

However, the conventional automatic breast pump lacking any massage function has failed to remove the breast stiffness with the following disadvantages:

1) With a switch on, an automatic breast pump has a continuous operation. A breast-milking mother cannot stop the operation of breast pump immediately, when her breast site feels painful through continual suction. Furthermore, when a switch is off, the switch operation is quite cumbersome.

2) Since the suction force is controlled by inflow air, the continuous operation of motor results in excessive electric consumption.

3) Since the main body of breast pump is directly attached to the upper part of human milk bottle, there is a high risk on the malfunction or internal contamination of breast pump.

4) Since the inside of human milk bottle cap is smeared with human milk flowing from the bottle via suction neck, the human milk bottle needs to be disinfected every time during use.

5) The conventional automatic breast pump lacking diverse functions has a simple suction without any massage function.

SUMMMARY OF THE INVENTION

To free from the aforementioned shortcomings, this invention relates to a breast pump which can perform the automatic suction with the following advantages:

1) A breast-milking mother can stop the operation of breast pump immediately, when her breast site feels painful through continual suction;

2) The suction can be immediately made available by re-pushing a switch, thus ensuring the convenience in use;

3) Since the breast pump has a massage function in addition to the basic suction of human milk, thus removing a breast stiffness in an efficient manner and improving the whole functions of breast pump;

4) Since a suction neck has a soft induction neck designed to softly contact with a breast site, a lactating woman feels comfort during use, and the rapid detachment of breast pump after use can be made through the fabrication of suction release value, thus making the separation procedure of breast pump easier;

5) Since the induction neck of breast pump is equipped with a separate induction conduit which is extended to the inside of a breast milk bottle, human milk can be directly dropped to the bottle, whereby any disinfection for bottle is unnecessary; and.

6) Since the breast milk bottle is connected to the main body of breast pump with a transparent hose, the insertion of breast pump to mother's nipple can be directly ascertained by naked eyes, thus preventing any smear in the bottle.

EXPLANATION OF MAJOR CODES IN THE DRAWINGS

| | |
|---|---|
| 10: Suction neck | 11: Cap |
| 12: Breast milk bottle | 13: Automatic pump |
| 14: Main body of breast pump | 15: Induction neck |
| 16: Tube | 16A: Milk-collecting neck |
| 17: Motor | 18: Pump body |
| 18A: Connection rod | 19: Suction neck |
| 20: Outlet | 21: Pump room |
| 22: Eccentric cam | 23: Power piece |
| 24: Massage plate | 25: Elastic piece |
| 26: Massage device | 27: Push button |
| 28: Valve case | 29: Suction neck |
| 30: Outlet | 31: Valve housing |
| 32: Valve slip | 33: Valve body |
| 34: Suction release value | 35: Tight lock plate |
| 36: Groove | 37: Induction conduit |
| 38: Contact switch | 39: Battery reservoir |
| 40: Battery cap | 41: Locking ring |
| 44: Tight seal ring | 45: Operational portion |
| 46: Suction valve | 47: Discharge valve |
| 48: Contact plate | 49: Lumbar portion |
| 50: Stopper piece | 51: Stopper groove |

DETAILED DESCRIPTION OF THE INVENTION

This invention is explained in detail based upon the accompanying drawings as set forth hereunder.

This invention is characterized by a breast pump 14 having a breast milk bottle 12 equipped with a suction neck 10 and cap 11, and the main body of a breast pump 14 including automatic pump 13, etc., wherein a soft induction neck 15 designed to softly cover a breast site is equipped to the breast milk bottle 12, while the breast milk bottle 12 and main body of said breast pump 14 are connected to a transparent tube 16 having a milk-collecting neck which can be housed or detached with a certain length.

In particular, this invention is characterized by a breast pump having an automatic pump 13 placed at the main body of breast pump, wherein it comprises a motor 17; a pump body 18 which is eccentrically combined to a shaft of the motor 17 vertically for rectilineal movement; a connection rod 18A formed in the pump body; suction neck 19 passing through the breast milk bottle and, a pump room having an outlet passing through the outer pathway.

Another embodiment of this invention is characterized by a breast pump, wherein the main body of said breast pump 14 is equipped with an eccentric cam 22 connected to the shaft of a motor 17; a motor piece 23 connected to said eccentric cam 22; massage plate which can be oscillated in a single coupling with the motor piece 23; and, a massage device 26 equipped with a recovery elastic piece 25 which is placed at the back side of said massage plate 24.

Another embodiment of this invention is characterized by a breast pump, wherein the main body of breast pump 14 comprises a manual push button 27; a valve case 28 fixing said push button 27 to the main body of breast pump 14; a value housing 31; a suction release valve 34 consisting of a valve body 33 which is installed in the inside of the valve housing 31 and a valve slip torn in a straight line.

Another embodiment of this invention is characterized by a breast pump, wherein said induction neck 15 comprises a tight-lock plate 35 in a trumpet form which can be tightly contacted to nipple site and its circumference; groove 36 which is placed on the back circumference of said tight-lock plate 35 and inserted to the front portion of said suction neck located at said breast milk bottle 12; and an induction conduit 37 which can be extended to the inside of said breast milk bottle in a certain length.

Another embodiment of this invention is characterized by a breast pump, wherein the automatic pump 13 is equipped with a contact switch 38 of three modes (stop, semi-automatic and automatic) which can be freely selected.

Another embodiment of this invention is characterized by a breast pump, wherein the main body of breast pump 14 is equipped with a battery reservoir 39, and battery cap 40 of the battery reservoir 39 is installed in a manner such that it can be opened and closed by a rotary locking and release mode.

This invention is explained in more detail based upon the accompanying drawings as set forth hereunder.

Figure 1:
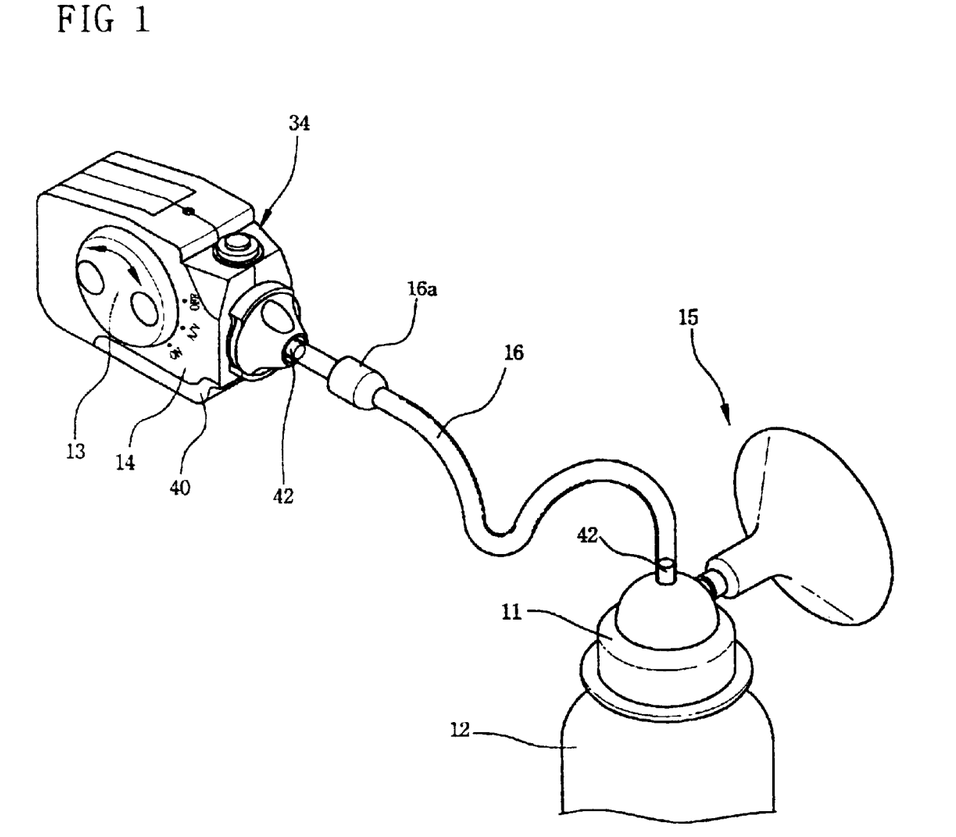
FIG. 1 is a perspective view showing the whole shape of breast pump according to this invention.

FIG. 1 is a perspective view showing the whole shape of breast pump according to this invention. The breast pump comprises the breast milk bottle 12 as a milk storage means; the main body of breast pump 14 including the automatic pump 13 as a power source to squeeze human milk; the tube 16 connecting both breast milk bottle 12 and automatic pump 13; and the milk-collecting neck is placed in the tube.

The tube 16 can be connected between a tube connection neck 42 formed in a cap 11 of breast milk bottle 12 and an upper part of the main body of breast pump, which can be easily housed and detached. Since the transparent tube can easily ascertain the inflow of human milk to the milk-collecting neck 16A and main body of breast pump 14 via the tube 16, there is no risk for the inflow of milk into the main body of breast pump 14 in the long run.

Figure 2:
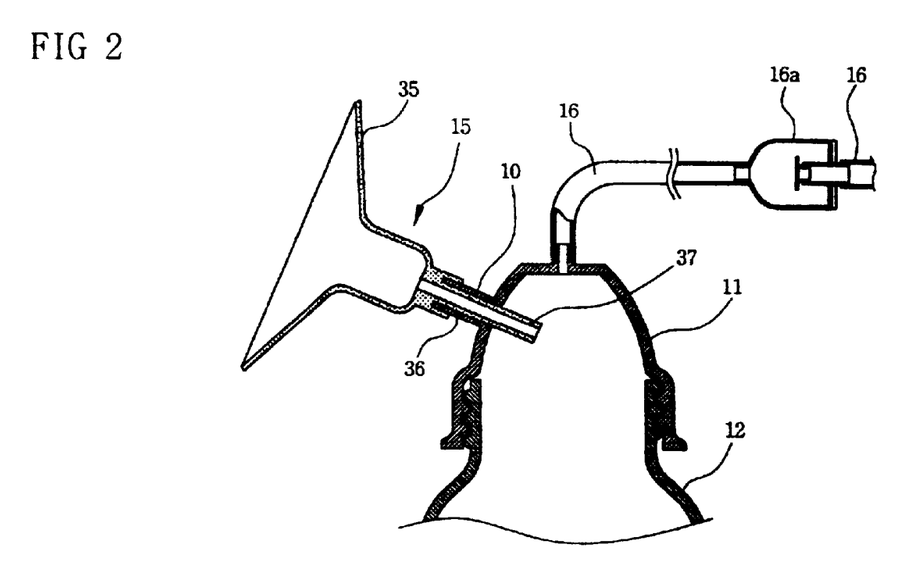
FIG. 2 is a sectional view showing that an induction neck is installed at human milk bottle from the breast pump.

FIG. 2 is a sectional view showing that an induction neck 15 is installed at the cap 11 of human milk bottle 12 from the breast pump.

The cap 11 at the breast milk bottle having the same structure of the general milk bottle may be freely connected and separated in a spiral form; the induction neck 15 is inserted to the suction neck 10 placed at the one-side of cap in a straight form The induction neck 15 comprises a tight lock plate in a trumpet form which can cover the front of a breast including nipple for its attachment; a groove 36 which can accurately connect the induction neck 15 and suction neck 10, since it is formed at the back circumference of tight lock plate 35 and inserted to the upper part of suction neck 10 at the breast milk bottle; and, a induction conduit 37 which is extended to the internal upper center of breast milk bottle 12 to let human milk drop into the breast milk bottle 12, thus preventing the smearing phenomenon of human milk in the inside of cap 11.

The induction neck 15 is installed in such a manner that it is inserted into the suction neck of breast milk bottle 12 via the groove 36. With the induction neck 15 constricted by vacuum force in the breast milk bottle 12, the outer air between the induction neck 15 and suction neck 10 is blocked, thus maintaining the vacuum state within the breast milk bottle 12 accurately.

In particular, since the whole induction neck 15 including the tight lock plate 35 is made from a soft material, the tight attachment of tight lock plate 35 to the front of a breast provides a soft feeling and comfort to a lactating woman, thus ensuring the convenience in use.

Figure 3:
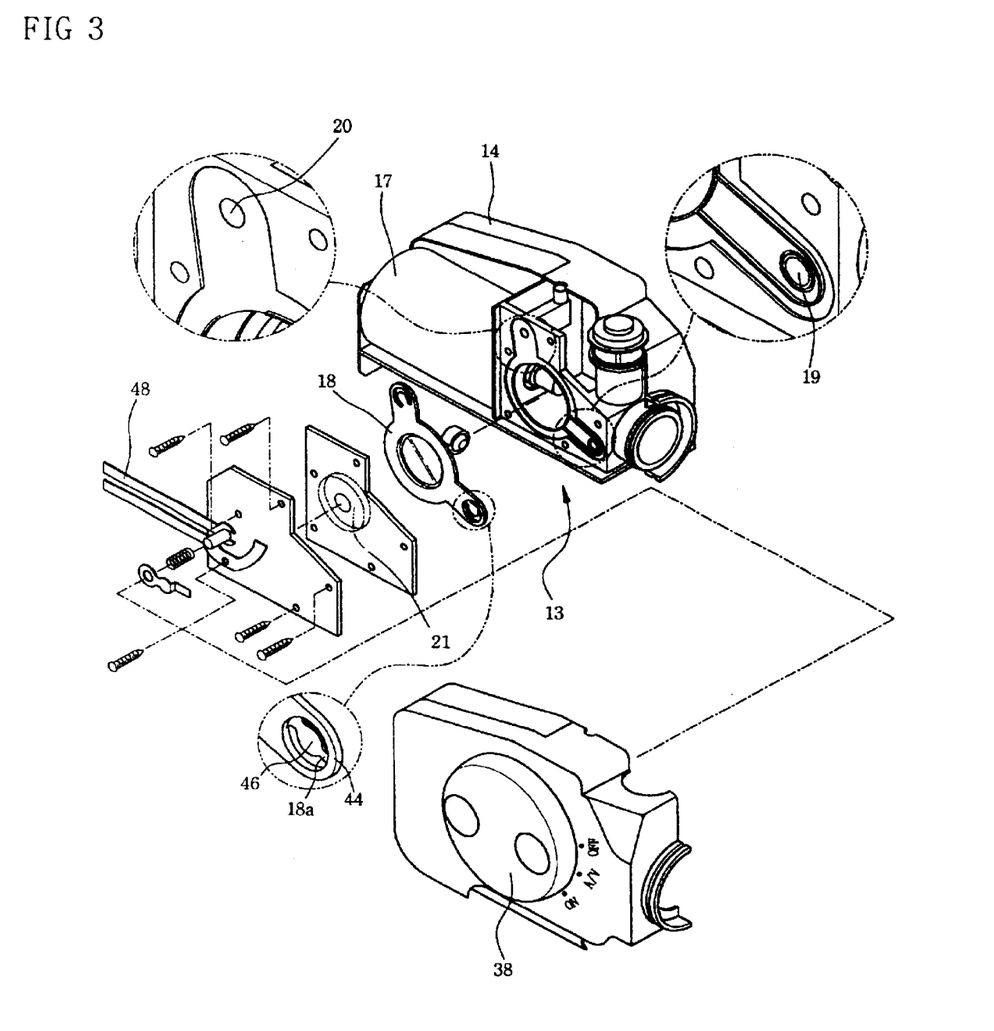
FIG. 3 is a perspective view showing the structure of automatic pump from the breast pump.

FIG. 3 is a perspective view showing the structure of automatic pump 13 from the breast pump according to this invention.

Figure 4A:
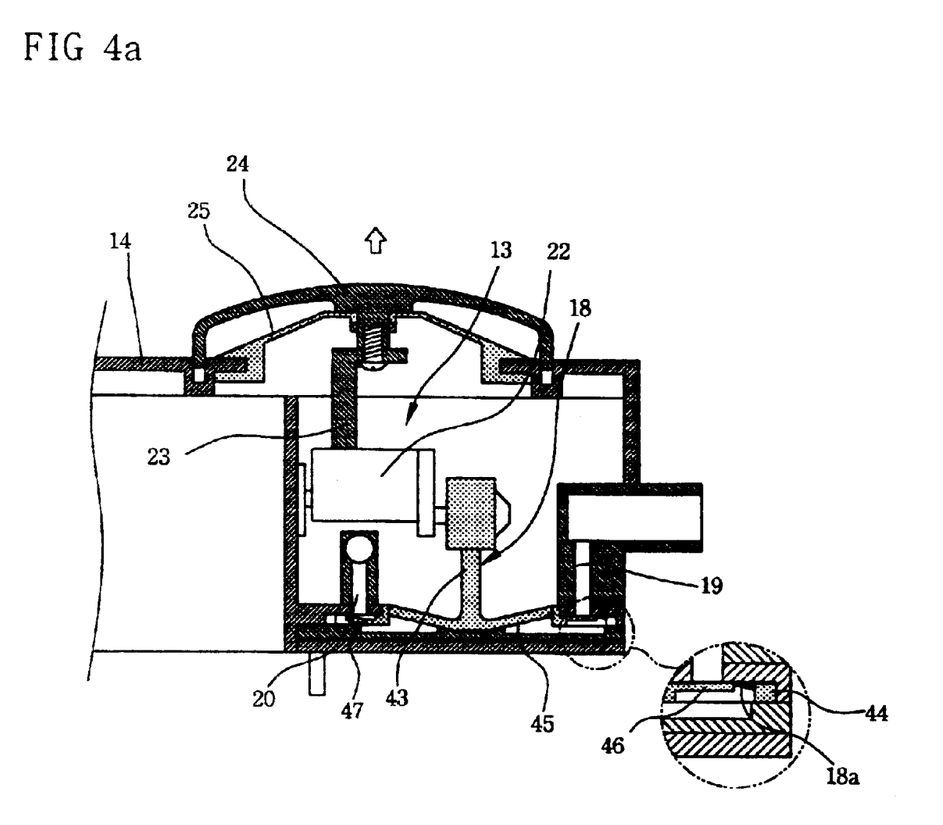
FIGS. 4a and 4b are sectional views showing the operational state of FIG. 3.
Figure 4B:
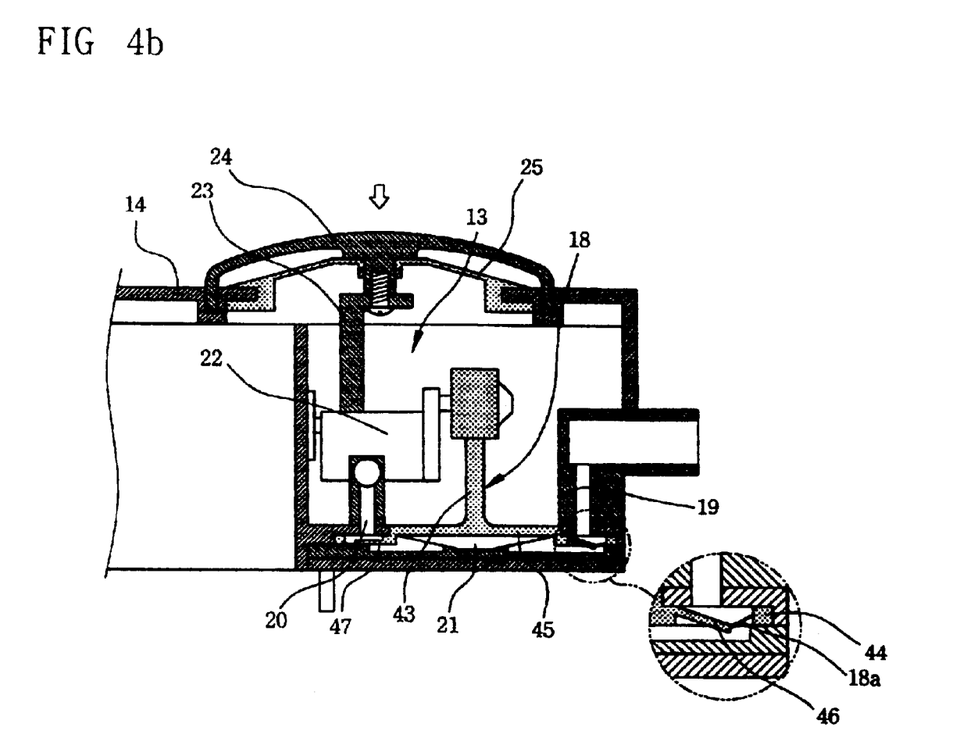

The automatic pump 13 is on or off by a separate switch means, wherein it comprises: a motor 17 installed within the inside of main body of breast pump 14; a pump body 18 which is eccentrically connected to the shaft of motor 17 to repeat the pumping, while making a rectilineal motion against the rotary movement of motor 17; an suction neck 19 passing through the breast milk bottle 12; and, a pump room having a certain space with the pump body 18, together with an outlet FIGS. 4a and 4b are sectional views showing the operational state of automatic pump 13.

The pump body 18, which plays an actual role in pumping, comprises a tight seal ring 44, an operational portion 45 and an operational rod 43 which is extended to backside in a certain length. Its pumping can be made by the operational rod which is eccentrically connected to the shaft of motor 17 to exchange a rotary motion into a rectilineal motion. The pump body 18 is equipped with a connection rod 18A which connects a suction valve at the suction neck 19 and tight seal ring 44, thus ensuring the tight-seal function of suction neck accurately.

As illustrated in FIG. 4a, the space of pump room 21 becomes widened due to suction of pump body 18 and then, the air within the breast milk bottle 12 is sucked by the suction neck 19. As illustrated in FIG. 4b, the space of pump room 21 becomes narrowed due to discharge of pump body 18 and then, the air within the pump room 21 is discharged by the outlet 20.

Both suction neck 19 and outlet 20 are equipped with a suction value 46 and discharge value 47, respectively. During the operation of pump body 18, the suction valve can suck the air within the breast milk bottle 12, while the discharge value can discharge the sucked air within the pump room 21 to the outside.

Further, this invention is characterized by a contact switch 38 as the switch means of automatic pump 13.

The automatic pump 13 is equipped with three modes (stop, semi-automatic and automatic) which can be freely selected, and a one-touch switch operation that is made available during semi-automatic operation.

As illustrated in FIG. 3, the automatic pump 13 includes two contact plates 48 that can be used to select a mode by rotating the contact switch 38.

From the contact switch 38, a mode is selected by a rib means at the rim circumference and a protracted stopper located at the main body of breast pump 14. In the case of semi-automatic mode, the repeated push-on, release-off may be made available due to the elasticity of the spring itself. In semi-automatic mode, the device is turned on by pressing the contact switch 38 by hand and turned off by the spring inside the device when releasing the pressing hand. In other words, in semi-automatic mode, the contact switch 38 can be turned on by pushing it and turned off by releasing it without pushing it again.

In the case of the semi-automatic mode, a lactating woman can squeeze her breast milk, by pushing the contact switch 38. When a lactating mother feels pain due to continual squeezing, she releases the pushed contact switch 38 to stop the suction of breast milk immediately. Thus, with the contact switch pushed, suction can be immediately made available, ensuring adequate control of suction during the squeeze operation of breast milking. The suction power control is to be done under the semi-automatic mode, and electricity is instantly disconnected when the required amount of suction is done. The suction power is maintained while the motor is be stopped. The suction power is weakened if outside air is penetrated even if the suction power is maintained while the motor is being stopped. By pressing the contact switch 38 slightly, the suction power can be enhanced. This function cannot be found in the prior breast pump inventions which can be turned on and off by only pushing or turning the switch. The motors in the prior breast pump inventions have to keep running to maintain the suction power because the prior art inventions are using separate suction power control switch and this speeds up the consumption of battery power; whereas the present invention minimizes battery power.

Figure 5:
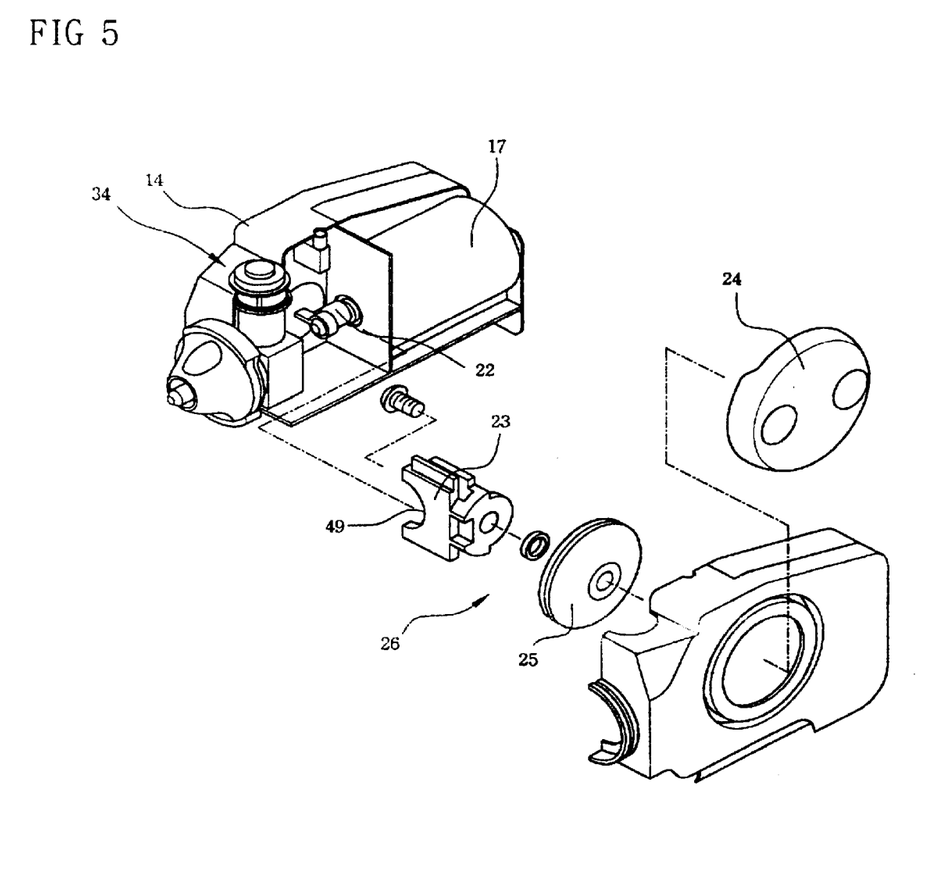
FIG. 5 a perspective view showing the structure of massage device from the breast pump.
Figure 6:
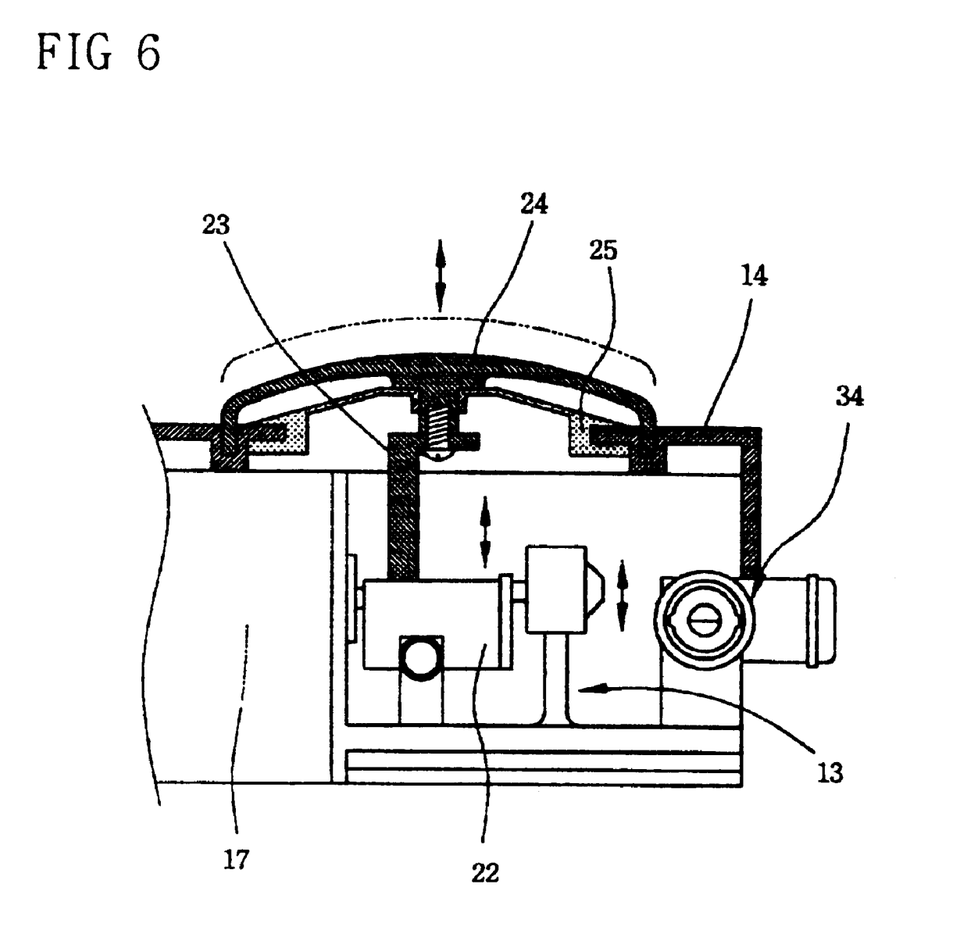
FIG. 6 is a sectional view of FIG. 5.

FIGS. 5 and 6 shows the structure of massage device from the breast pump of this invention.

The massage device 26 comprises an eccentric cam 22 which is connected to the shaft of a motor 17 for possible rotation; an operation piece 23 connected to the eccentric cam 22 using a lumbar portion 49 in a half-circle form; massage plate 24 which can be oscillated in a single coupling with said operation piece 23; and, a recovery elastic piece 25 where the rim of main body of breast pump is fixed and placed at the back side of massage plate 24 to provide the massage plate with a recovery force.

FIG. 4A shows that the massage plate 24 is pushed upward by the eccentric cam 22. FIG. 4B shows that the massage plate 24 is moved downward. When the massage plate 24 is turned to a certain place during the automatic mode of contact switch 38, the power piece 23, being contacted with the eccentric cam 22 rotated by motor 17, can be repeatedly moved upward and downward. Then, the massage plate 24, being connected with the power piece in a single coupling, is repeatedly oscillated, thus ensuring the massage by the vibration of the massage plate against a stiff breast.

Figure 7:
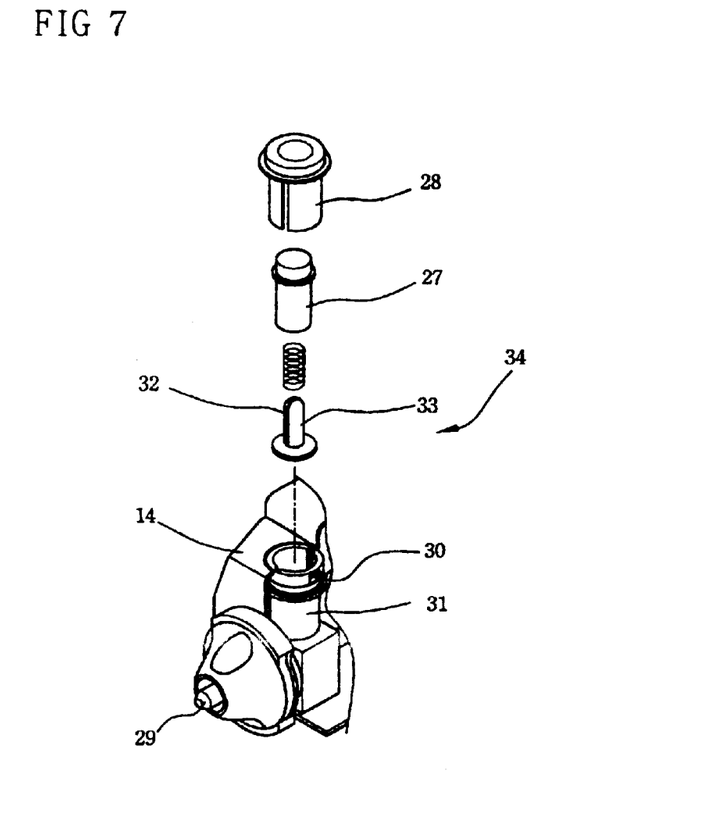
FIG. 7 is a perspective view showing the structure of suction release valve from the breast pump.

FIG. 7 is a perspective view showing the structure of suction release valve 34 from the breast pump.

The suction release valve 34 comprises a manual push button 27 which widens the valve slip 32 of valve body 33 and a spring means which recovers the widened valve slip of 32; a valve case 28 which fixes the push button 27 to the main body of breast pump 14; a valve housing 31 which is jointly passed with a suction neck 29 at the main body of breast pump 17 and at the same time, equipped with a plural number of outlets 30; and, a valve body 33 which is installed in the valve housing 31 to block the suction part of valve housing 31 and outer part, while having a silicon-type elastic valve slip cut in a vertical straight line.

After completing the squeeze of breast milk, the suction release valve 34 serves to remove the vacuum state of breast milk bottle 12 and adsorption state of induction neck 15.

To this end, with the push button 27, its lower end pushes the upper end of valve body 33 equipped with the valve slip 32; simultaneously, when the valve slip 32 is widened, the outer air flows into the inside of breast milk bottle from the suction neck 29 of main body of breast pump 14 and tube 16, the induction neck may be easily detached from the front breast, while removing the vacuum state of breast milk bottle 12.

With the push button released, the tight-seal state can be again acquired, since the operation of breast pump is in an original state.

Figure 8:
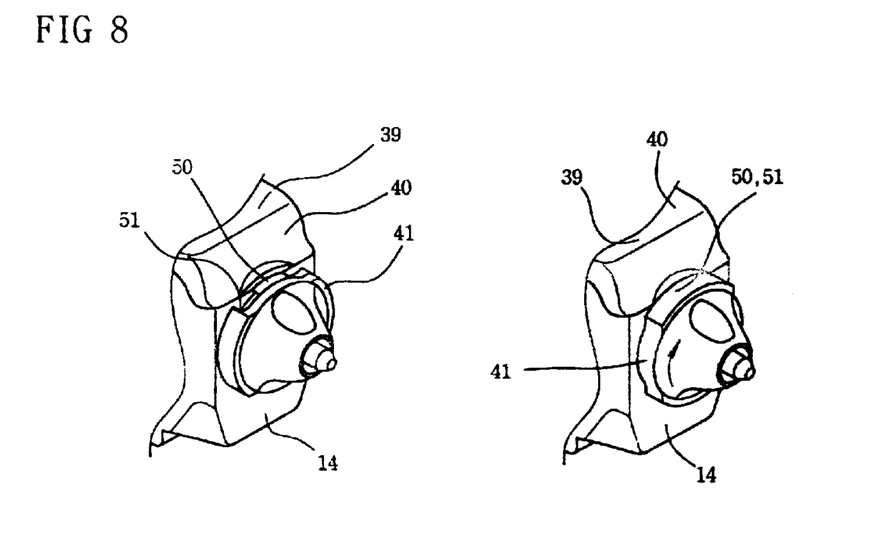
FIG. 8 a perspective view showing the locking/release structure of battery cap from the breast pump.

FIG. 8 is a perspective view showing the locking/release structure of the battery cap of the breast pump.

The breast pump of this invention can be used by connecting it with an electric cord.

When the breast pump is used by connecting it to an electric cord, a separate jack is provided, together with a battery reservoir 39.

When a battery cap 40 is opened or closed, a locking ring installed at the upper part of main body of breast pump 14 is operated.

More specifically, since the locking ring 41 is equipped with a long stopper groove 51 which can connect with a stopper piece 50 installed at the battery cap, the locking ring is turned to one side to deviate it from the stopper groove 51, as shown in the left drawing, or to connect with the stopper groove, as shown in the right drawing of FIG 8. Since the battery cap 40 is easily opened or closed, the breast pump does not need to be detached while exchanging a battery. The locking device in the battery cap 40 prevents the battery cap from falling apart when hit by an outside force and makes it easy to open and close. (In prior inventions, the battery cap was easily opened when it falls or is hit by an outside force since there is no locking device.

As described above, to be free from some drawbacks that a conventional manual or automatic breast pump has, this invention relates to a breast pump which can perform automatic suction with the following advantages:

1) The suction mode such as automatic or semi-automatic function can be freely selected;

2) The additional massage function can contribute much to removal of any breast stiffness;

3) The suction neck of breast pump has a soft induction neck, while the breast pump can be easily detached using a suction release valve; and, 4) Since the breast milk bottle is connected to the main body of the breast pump with a transparent hose having a milk-collection neck, any human milk can be prevented from flowing into the inside of the automatic pump, thus avoiding any malfunction of automatic pump and providing comfort during suction.

What is claimed is:

1. A breast pump having a breast milk bottle equipped with a suction neck and cap, and the main body of a breast pump including automatic pump, wherein the main body of said pump is equipped with an eccentric cam connected to the shaft of a motor; an operation piece connected to said eccentric cam; a massage device comprising a massage plate which can be oscillated in a single coupling with said motor piece and a recovery elastic piece which is placed at the back side of said massage plate.

2. The breast pump according to claim 1, wherein a soft induction neck is attached to said breast milk bottle, and said breast milk bottle and main body of breast pump are connected to a transparent tube which can be housed and detached with a certain length so as to install a milk-collecting neck.

3. The breast pump according to claim 1, wherein said automatic pump is equipped with three modes which can be freely selected, and a contact switch is further installed for one-touch switch-on and switch-off during semi-automatic operation.

4. The breast pump according to claim 2, wherein said induction neck comprises a tight-lock plate in a trumpet form which can be tightly contacted to nipple site and its circumference; groove which is placed on the back circumference of said tight-lock plate and inserted to the front portion of said suction neck located at said breast milk bottle; and an induction conduit which can be extended to the inside of said breast milk bottle in a certain length.

5. The breast pump according to claim 1, wherein the main body of said breast pump comprises a manual push button; a valve case fixing said push button to the main body of breast pump; a valve housing; a suction release valve consisting of a valve body which is installed in the valve housing and a valve slip cut in a vertical straight line.

6. The breast pump according to claim 1, wherein the main body of said breast pump is equipped with a battery reservoir, and battery cap of said battery reservoir release mode.

7. The breast pump according to claim 1, wherein a pump body installed at said automatic pump is equipped with a connection rod connecting a ring and a suction valve.

* * * * *

UNITED STATES PATENT AND TRADEMARK OFFICE
CERTIFICATE OF CORRECTION

PATENT NO.    : 6,500,143 B2
DATED         : December 31, 2002
INVENTOR(S)   : Kyoung Duk Suh It is certified that error appears in the above-identified patent and that said Letters Patent is hereby corrected as shown below:

<u>Column 8,</u>
Line 18, between "reservoir" and "release", add -- is installed in a manner such that it can be opened and closed by a rotary locking and --.

Signed and Sealed this

Third Day of June, 2003

JAMES E. ROGAN
*Director of the United States Patent and Trademark Office*